US012440347B2

(12) United States Patent
Valkoun et al.

(10) Patent No.: US 12,440,347 B2
(45) Date of Patent: Oct. 14, 2025

(54) EXPANDABLE ARTICULATING TRANSFORAMINAL LUMBAR INTERBODY SPACER

(71) Applicant: Astura Medical Inc., Iriving, TX (US)

(72) Inventors: Anthony Valkoun, Irving, TX (US); Thomas Purcell, Irving, TX (US)

(73) Assignee: ASTURA MEDICAL INC, Irving, TX (US)

( * ) Notice: Subject to any disclaimer, the term of this patent is extended or adjusted under 35 U.S.C. 154(b) by 115 days.

(21) Appl. No.: 18/378,653

(22) Filed: Oct. 11, 2023

(65) Prior Publication Data

US 2025/0120820 A1 Apr. 17, 2025

Related U.S. Application Data

(60) Provisional application No. 63/414,820, filed on Oct. 10, 2022.

(51) Int. Cl.
*A61F 2/44* (2006.01)
*A61F 2/30* (2006.01)

(52) U.S. Cl.
CPC .. *A61F 2/4455* (2013.01); *A61F 2002/30433* (2013.01)

(58) Field of Classification Search
CPC ...... A61F 2/442; A61F 2/4425; A61F 2/4455; A61F 2002/443
USPC ............................................ 623/17.11–17.16
See application file for complete search history.

(56) References Cited

U.S. PATENT DOCUMENTS

| | | | | |
|---|---|---|---|---|
| 11,737,889 B2 * | 8/2023 | Dewey | A61F 2/4611 | 623/17.15 |
| 11,752,009 B2 * | 9/2023 | Melchor | A61F 2/4455 | 623/17.11 |
| 2013/0158664 A1 * | 6/2013 | Palmatier | A61F 2/4425 | 623/17.16 |
| 2014/0180421 A1 * | 6/2014 | Glerum | A61F 2/447 | 623/17.15 |
| 2014/0236297 A1 * | 8/2014 | Iott | A61F 2/447 | 623/17.15 |
| 2014/0249631 A1 * | 9/2014 | Weiman | A61F 2/447 | 623/17.16 |
| 2014/0277497 A1 | 9/2014 | Bennett et al. | | |
| 2015/0366675 A1 * | 12/2015 | Matthews | A61F 2/30771 | 623/17.16 |
| 2015/0374507 A1 * | 12/2015 | Wolters | A61B 17/8858 | 623/17.15 |
| 2021/0369466 A1 | 12/2021 | Valkoun et al. | | |

FOREIGN PATENT DOCUMENTS

WO WO2014005154 A1 1/2014

OTHER PUBLICATIONS

International Search Report and Written Opinion in PCT Application No. PCT/US2023/034866 dated Mar. 1, 2024.

* cited by examiner

*Primary Examiner* — Jacqueline T Johanas
*Assistant Examiner* — Christina Negrellirodriguez
(74) *Attorney, Agent, or Firm* — Michael R Shevlin

(57) ABSTRACT

An expandable interbody spacer for placement between adjacent vertebrae having two or more upper and lower endplates and lateral expansion wedges configured to couple a drive means to expand both a height and a width of the expandable interbody spacer from a collapsed state to an expanded state.

3 Claims, 7 Drawing Sheets

EXPANDABLE ARTICULATING TRANSFORAMINAL LUMBAR INTERBODY SPACER

CROSS-REFERENCE TO RELATED APPLICATIONS

This application claims the benefit of U.S. Provisional Application No. 63/414,820 filed Oct. 10, 2022, which is incorporated herein by reference.

FIELD

The present invention relates generally to the field of surgery, and more specifically, to an expandable intervertebral body fusion device (i.e., "interbody spacer") for placement in intervertebral space between adjacent vertebrae.

BACKGROUND

A spinal disc can become damaged as a result of degeneration, dysfunction, disease and/or trauma. Conservative treatment can include non-operative treatment through exercise and/or pain relievers to deal with the pain. In surgical treatments, interbody spacers may be used between adjacent vertebra, resulting in spinal fusion of the adjacent vertebra. Treatment options include disc removal and replacement using an interbody spacer such as anterior cervical interbody fusion (ACIF), anterior lumbar interbody fusion (ALIF), direct lateral interbody fusion (DLIF) (also known as XLIF), posterior lumbar interbody fusion (PLIF), and transforaminal lumbar interbody fusion (TLIF).

A fusion is a surgical method wherein two or more vertebrae are joined together (fused) by way of interbody spacers, sometimes with bone grafting, to form a single bone. The current standard of care for interbody fusion requires surgical removal of all or a portion of the intervertebral disc. After removal of the intervertebral disc, the interbody spacer is implanted in the interspace.

Interbody spacers must be inserted into the intervertebral space in the same dimensions as desired to occupy the intervertebral space after the disc is removed. This requires that an opening sufficient to allow the interbody spacer must be created through surrounding tissue to permit the interbody spacer to be inserted into the intervertebral space. In some cases, the intervertebral space may collapse prior to insertion of the interbody spacer. In these cases, additional hardware may be required to increase the intervertebral space prior to insertion of the implant.

In addition, minimally invasive surgical techniques may have been used on the spine. Under minimally invasive techniques, small incisions are done to access the intervertebral space. Through these incisions, discs are removed and an interbody spacer is placed in the intervertebral disc space to restore normal disc height. Minimally invasive spine surgery offers multiple advantages as compared to open surgery. Advantages include: minimal tissue damage, minimal blood loss, smaller incisions and scars, minimal post-operative discomfort, and relative quick recovery time and return to normal function.

Typical expandable implants utilize angled ramps in conjunction with slots or t-rails and a separate drive screw to compress the mechanism and force expansion. This type of mechanism limits the available expansion of the implant due to the amount of material required to house the slots or t-rails. Typically, the expansion ramp is not able to pass the midline of the part. In addition, this mechanism is typically limited to a single plane of expansion (I.E., height or width).

Current expandable implants are typically expensive and difficult to manufacture due to the complexity of the expansion mechanism and the available manufacturing techniques require the size and positional tolerance of these features to be relatively loose to allow for manufacturability. In addition, this type of mechanism limits the available expansion of the interbody spacer due to the amount of material required to house the slots and/or t-rails.

It would be desirable to develop an easy to manufacture expandable interbody spacer that can be inserted into the intervertebral space at a first smaller dimension and once in place, deploy to a second, larger dimension.

SUMMARY

Disclosed is an expandable interbody spacer that is configured to have an initial collapsed state having a first height and first width suitable for being inserted into an intervertebral space defined by a pair of adjacent vertebrae, and a final expanded state having a second height and second width that is greater than the first height. The expandable interbody spacer may be expanded from the initial collapsed state to the expanded state in-situ. The expanded state increases the distance between the adjacent vertebrae and provides support to the adjacent vertebrae while bone fusion occurs and also provides rigid support between the adjacent vertebrae that withstands compressive forces. By inserting the expandable interbody spacer into the intervertebral space in the initial collapsed state, it is possible to perform the surgery percutaneously with minimal disruption to tissues surrounding the surgical site and intervening soft tissue structures.

DETAILED DESCRIPTION

The interbody spacer disclosed is for a transforaminal lumbar interbody fusion (TLIF) but the same features may be used for anterior cervical interbody fusion (ACIF), anterior lumbar interbody fusion (ALIF), direct lateral interbody fusion (DLIF) (also known as XLIF), and posterior lumbar interbody fusion (PLIF). The expandable interbody spacer includes a collapsed state and expanded state. The collapsed state allows insertion between the adjacent vertebrae with minimal dimensions. The expandable interbody spacer expands both vertically and laterally by means of single-angle ramps and rails. Upper and lower endplates single-angle ramps and rails to move the upper and lower endplates both laterally and vertically away from each other. The endplates may also be textured to promote bony integration.

Figure 1:
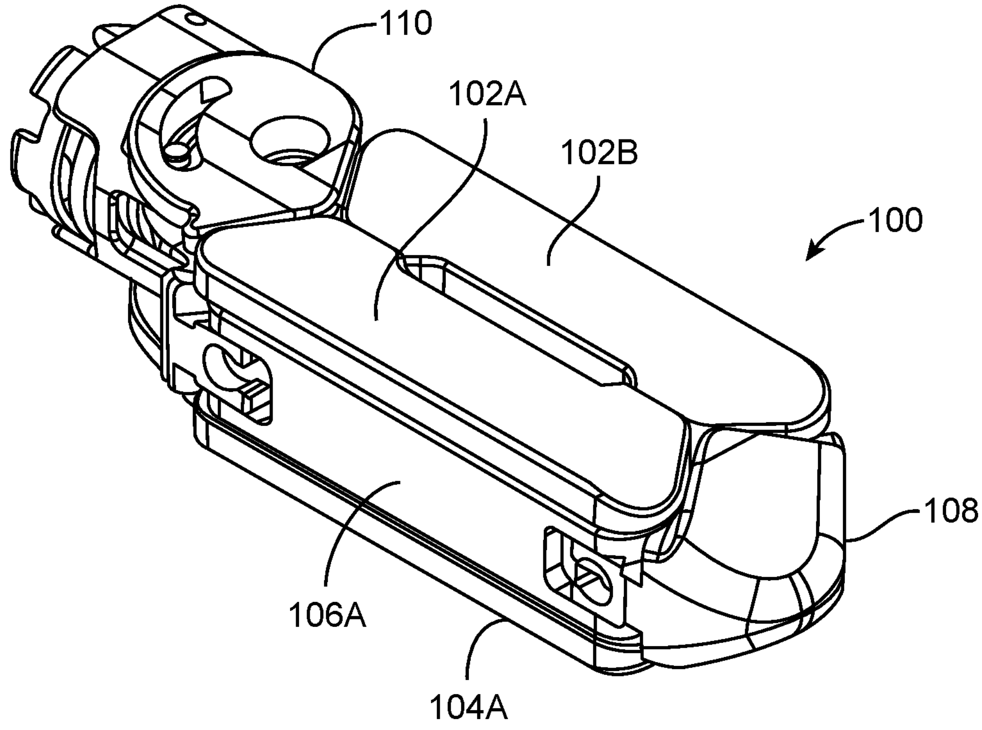
FIG. 1 is a perspective view of an expandable articulating transforaminal lumbar interbody spacer in a collapsed state for introduction into disc space.

FIG. 1 is a front perspective view of an expandable articulating transforaminal lumbar interbody spacer 100 ("expandable interbody spacer 100") that consists of 17 primary components, a frame, a housing, two lateral expansion wedges (anterior and posterior lateral expansion wedges), four vertical expansion shuttles (two anterior and two posterior vertical expansion shuttles), a drive nut, a drive screw, an articulation component, two pivot pins, four endplates (two upper and two lower endplates). The frame and housing both contain single angled ramps intended to induce lateral expansion. The four endplates contain single angle rails intended to mate with the four vertical expansion shuttles. The four vertical expansion shuttles are captured within the two lateral expansion wedges and contain a D-rail profile that mates with either the frame or housing, which allow for mechanical collapse of the implant.

The housing and frame are positioned relative to each other via the two lateral expansion wedges and a central strut of the frame. The central strut contains an angled slot that is engaged with the drive screw via two pivot pins. The drive screw is captured within the articulation component which is rotatably engaged with the housing via radial slots. Advancing the drive nut causes the drive screw to translate rearward relative to the housing. This causes the two pivot pins to engage the frame slot and induce axial compression of the frame relative to the housing via two different methods. When the articulation component is in the axial state the pivot pins will contact the frame slot at such an angle as to produce direct axial translation. When the articulation component is in the articulated state, or any state between the axial state and the max articulation state, the pivot pins will instead contact the angled face of the frame slot. The translation of the pins along this angled face will induce axial compression of the frame relative to the housing. This axial compression forces the two lateral expansion wedges to interact with the angled ramps contained within the frame and housing, forcing lateral expansion of the four endplates and four vertical expansion shuttles. Simultaneously the frame and housing induce axial translation on the four vertical expansion shuttles inducing vertical expansion of the four endplates via the railed interface between the four vertical expansion shuttles and four endplates.

Typical expandable implants utilize compound angled ramps in conjunction with slots or t-rails and a separate drive screw to compress the mechanism and force expansion. This type of mechanism limits the available expansion of the implant due to the amount of material required to house the compound angled slots and/or t-rails. In addition, this mechanism typically limits maximum possible expansion due to the fact that the rail mechanism is not able to pass the midline of the part, limiting available rail length to 50% of the implant height at maximum.

By comparison, by utilizing single angle rails in conjunction with 'stacking' the mechanism expandable interbody spacer 100 is able to achieve significantly more rail engagement while also adding additional vertical support elements to the upper and lower endplates in the expanded state. In addition, the utilization of L-rails in a staggered configuration allows for the expansion mechanism to exceed the midline of the part, this additional ramp length allows for increased implant expansion beyond what is typically available for any given implant footprint.

The expandable interbody spacer 100 also allows for a variation of lordotic angles for the anterior/posterior vertical expansion shuttles and respective anterior/posterior endplates. Via the varying of this angle, the expandable interbody spacer 100 is able to induce different rates of vertical expansion while maintaining symmetrical lateral expansion. The varying vertical expansion rate during expansion can be utilized to induce lordosis within the expandable interbody spacer 100.

The articulation portion of the proposed concept allows for expansion to be induced at any point in the articulation state. This is achieved via the angled ramp and pivot pin mechanism, when in the axial state the pivot pins will contact the slot at such an angle as to produce direct axial translation. While in the articulated state or any state between axial and max articulation the pivot pins will instead contact the angled face of the slot, which via the angle creates axial translation of the housing relative to the frame. In addition, the utilization of a nitinol retention pin in conjunction with machined flats on the expansion nut allow for automatic expansion locking at all expansion states.

Referring again to FIG. 1. the expandable interbody spacer 100 is shown in a collapsed state having posterior and anterior upper endplates 102A, 102B, posterior and anterior lower endplates 104A, 104B, posterior and anterior lateral expansion wedges 106A, 106B, a frame 108 and a housing 110. The frame 108 is positioned on a front end of the expandable interbody spacer 100 and the housing 110 is positioned on a rear end of the expandable interbody spacer 100.

Figure 2:
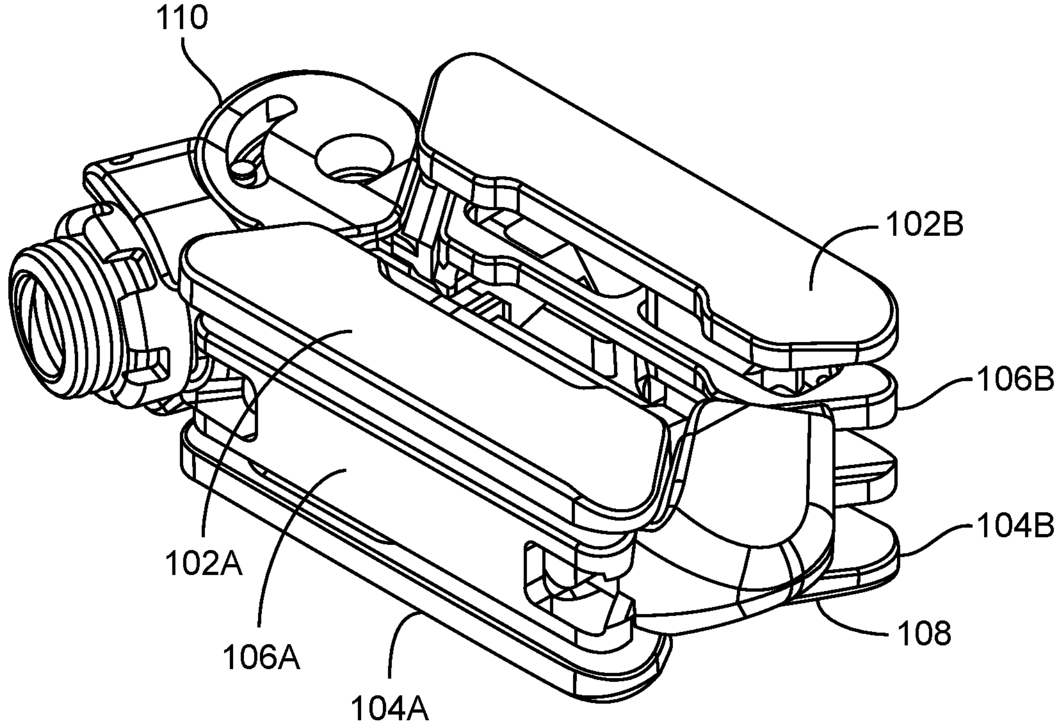
FIG. 2 is a perspective view showing the expandable interbody spacer of FIG. 1 in an expanded state.

FIG. 2 is a perspective view of the expandable interbody spacer 100 in an expanded state. During expansion, the expandable interbody spacer 100 expands both vertically and laterally, changing the vertical height V and lateral width L from a collapsed state to expanded state. Changing the vertical height V and lateral width L includes the posterior and anterior upper endplates 102A, 102B and posterior and anterior lower endplates 104A, 104B simultaneously expanding both vertically and laterally away from each other, and the posterior and anterior lateral expansion wedges 106A, 106B expanding laterally away from each other.

During vertical expansion, the posterior and anterior upper endplates 102A, 102B and the posterior and anterior lower endplates 104A, 104B expand vertically V from each other. During lateral expansion, the posterior upper and lower endplates 102A, 104A on one side expand laterally L1 away from the anterior upper and lower endplates 102B, 104B on the other side, and the lateral expansion wedges 106A, 106B expand laterally L2 away from each other.

Figure 3:
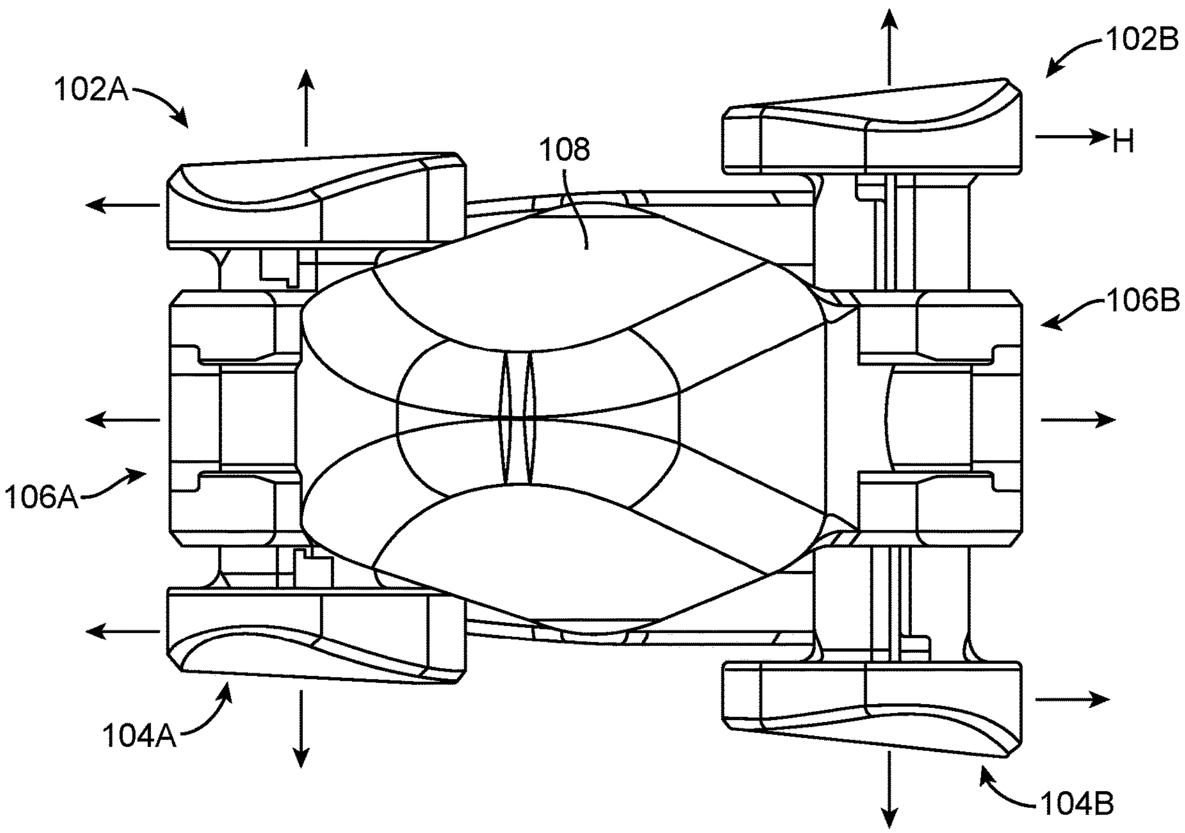
FIG. 3 is a front view of the expandable interbody spacer of FIG. 1.

FIG. 3 is a front view of the expandable interbody spacer 100 in the expanded state with the posterior and anterior upper and lower endplates 102A, 102B, 104A, 104B expanded both vertically and laterally from each other, and the posterior and anterior lateral expansion wedges 106A, 106B expanded laterally away from each other.

Figure 4:
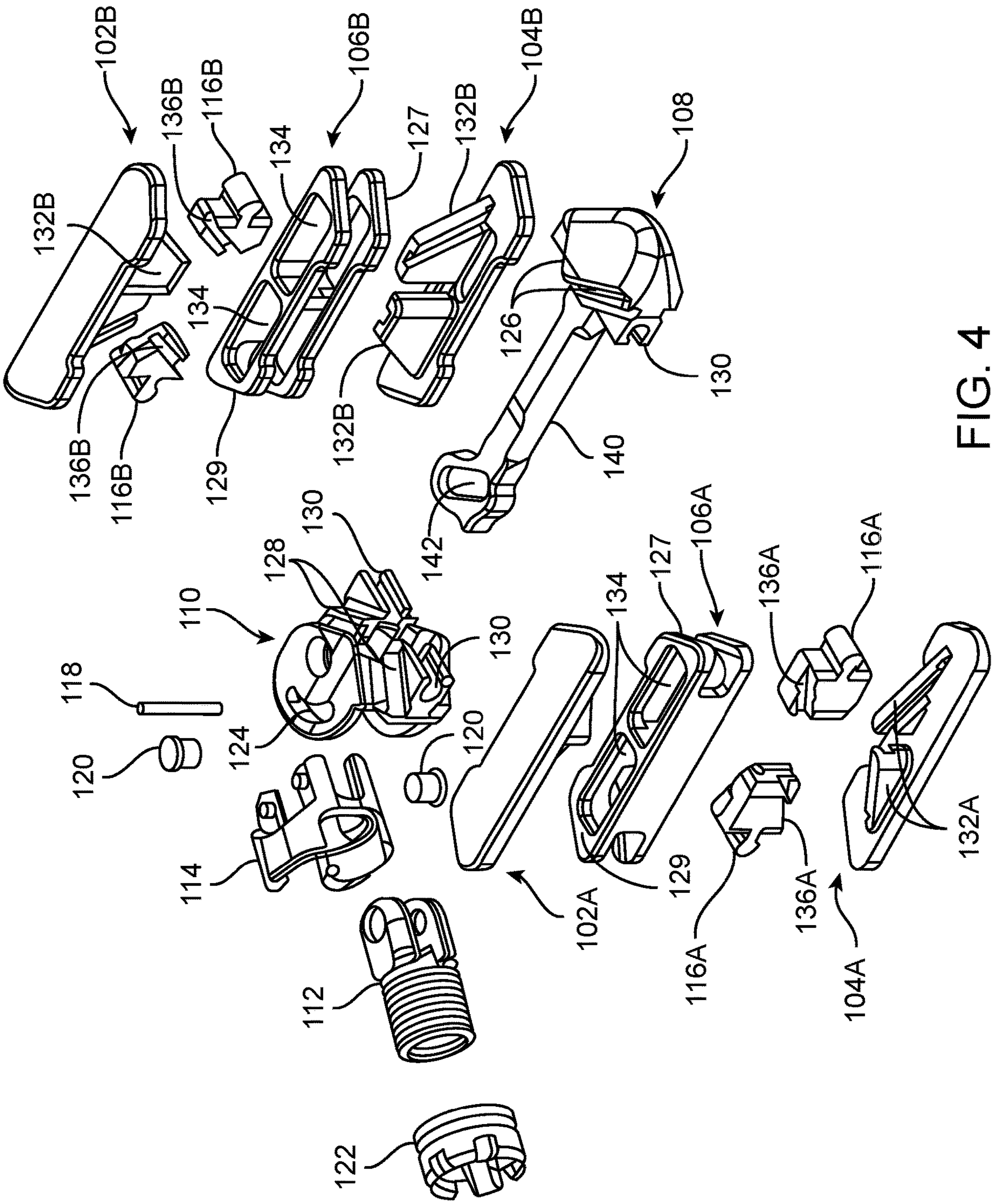
FIG. 4 is an exploded perspective view of the expandable interbody spacer.

FIG. 4 is an exploded perspective front view of the expandable interbody spacer 100 showing the components, including the posterior and anterior upper endplates 102A, 102B, the posterior and anterior lower endplates 104A, 104B, the posterior and anterior lateral expansion wedges 106A, 106B, the frame 108, the housing 110, the drive screw 112, the articulation component 114 and the drive nut 122. Also shown are right and left vertical expansion shuttles 116A, 116B, retention pin 118, and pivot pins 120.

The expandable interbody spacer 100 also allows for a variation of posterior and anterior angles for the vertical expansion shuttles 116A, 116B and respective upper and lower endplates 102A, 102B, 104A, 104B endplates. Via the varying of this angle, one is able to induce different rates of vertical expansion between the posterior upper and lower endplates 102A, 104A and the anterior upper and lower 102B, 104B endplates, while maintaining symmetrical lateral expansion posterior 102A, 104A and anterior endplates 102B, 104B. The varying vertical expansion rate between the posterior end plates and the anterior endplates can be utilized to induce lordosis within the expandable interbody spacer 100 as it is expanded.

The articulation of the expandable interbody spacer 100 allows for expansion to be induced at any point in the articulation state. This is achieved via the angled frame slot 142 and pivot pin mechanism 120, when in the axial state the pivot pins 120 will contact the angled frame slot 142 at such an angle as to produce direct axial translation. While in the articulated state, or any state between axial and max articulation, the pivot pins 120 will instead contact the angled face of the angled frame slot 142, which via the angle creates axial translation of the housing 110 relative to the frame 108. In addition, the utilization of a nitinol retention pin 118 in conjunction with machined flats on the expansion nut 122 allow for automatic expansion locking at all expansion states.

The frame 108 includes angled ramps 126 configured to interact with angled ramp ends 127 during expansion, and the housing 110 includes angled ramps 128 configured to interact with angled ramp ends 129 of the posterior and anterior lateral expansion wedges 106A, 106B during expansion. In some embodiments, the angled ramps 126, 128 are single-angle ramps configured to induce lateral expansion of the posterior and anterior lateral expansion wedges 106A, 106B.

The frame 108 and the housing 110 further include lateral slots 130 configured to engage D-rail profile protrusions on the posterior and anterior vertical expansion shuttles 116A, 116B for lateral expansion.

The upper and lower endplates 102A, 102B, 104A, 104B include ramped features 132A, 132B that fit through upper and lower openings 134 in the lateral expansion wedges 106A, 106B. The ramped features 132A, 132B are configured to engage corresponding ramps 136A, 136B on vertical expansion shuttles 116A, 116B. In some embodiments, the ramped features 132A, 132B and vertical expansion shuttle ramps 136A, 136B are single-angle rails that induce vertical expansion of the upper and lower endplates 102A, 102B, 104A, 104B.

The vertical expansion shuttles 116A, 116B. may be captured within inward facing slots of the lateral expansion wedges 106A, 106B proximate the upper and lower openings 134.

Figure 5:
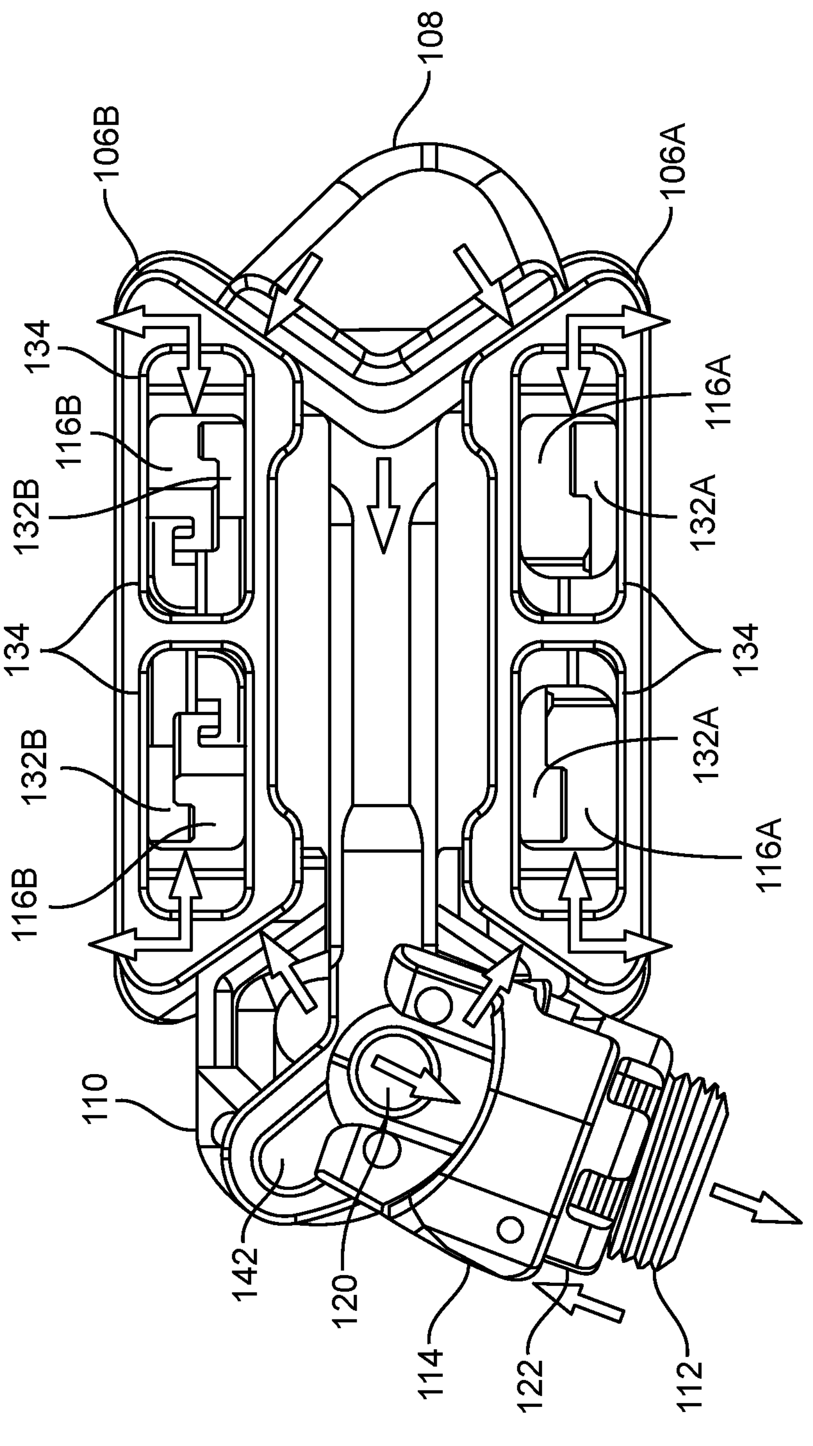
FIG. 5 is a top view showing the expandable interbody spacer in an expanded state without the upper endplates.

FIG. 5 is a top view showing the assembled expandable interbody spacer 100 in the expanded state without the upper endplates 102A, 102B. In the embodiment shown, the drive screw 112 is in the articulated state and the pivot pins 120 are engaged with the angled face of the angled frame slot 142.

The vertical expansion shuttles 116A, 116B are captured within the lateral expansion wedges 106A, 106B and the ramp features 132A, 132B of the upper and lower endplates 102A, 102B, 104A, 104B are positioned within the upper and lower openings 134. The vertical expansion shuttles 116A, 116B are engaged with the lateral slots 130 of the frame 108 and the housing 110, and the ramps 136A, 136B are engaged with the ramp features 132A, 132B of the endplates 102A, 102B, 104A, 104B.

Referring back to FIG. 2, the frame 108 and housing 110 are positioned relative to each other via the posterior and anterior lateral expansion wedges 106A, 106B and a central strut 140 of the frame 108. The central strut 140 contains the angled frame slot 142 that is engaged with the drive screw 112 via two pivot pins 120. The drive screw 112 is captured within the articulation component 114 which is rotatably engaged with the housing 110 via radial slots 124. Advancing a drive nut 122 causes the drive screw 112 to translate rearward relative to the housing 110. This causes the two pivot pins 120 to engage the angled frame slot 142 and induce axial compression of the frame 108 relative to the housing 110 via two different methods. When the articulation component 114 is in the axial state, the pivot pins 120 will contact the angled frame slot 142 at such an angle as to produce direct axial translation. When the articulation component 114 is in the articulated state, or any state between the axial state and the max articulation state, the pivot pins 120 will instead contact the angled face of the angled frame slot 142. The translation of the pivot pins 120 along this angled face will induce axial compression of the frame 108 relative to the housing 110. This translation forces the posterior and anterior lateral expansion wedges 106A, 106B to interact with the angled ramps 126, 128 of the frame 108 and housing 110 to induce lateral translation of the posterior and anterior vertical expansion shuttles 116A, 116B and lateral expansion of the posterior upper and lower endplates 102A, 104A away from the anterior upper and lower endplates 102B 104B endplates.

Simultaneously the frame 108 and housing 110 induce axial translation on the posterior and anterior vertical expansion shuttles 116A, 116B inducing vertical expansion of the upper end plates 102A, 102B from the lower end plates 104A, 104B endplates via the railed interface between the vertical expansion shuttles 116A, 116B and upper and lower endplates 102A, 102B, 104A, 104B.

When the drive screw 112 is rotated in a second direction, the frame 108 and housing 110 move away from each other and the right and left components move toward each other, going from an expanded state to a collapsed state.

Figure 6A:
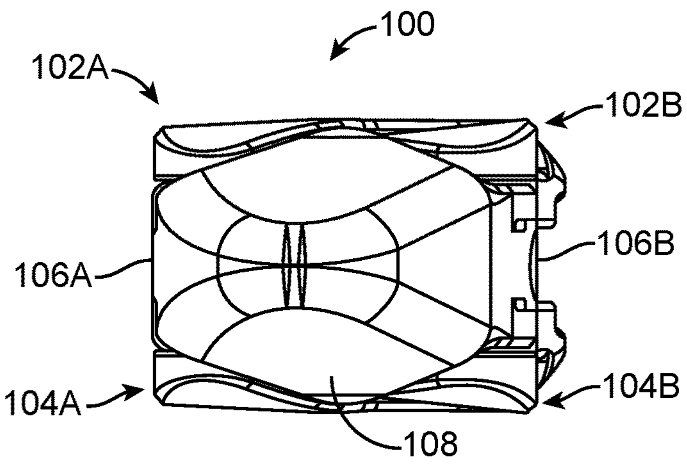
FIGS. 6A-6C show a front view, a side view and a top view of the expandable interbody spacer of FIG. 1 in the collapsed state.

FIG. 6A is a front view of the expandable interbody spacer 100 in the collapsed state showing the, the upper and lower endplates 102A, 104A, the lateral expansion wedges 106A, 106B, and the frame 108.

Figure 6B:
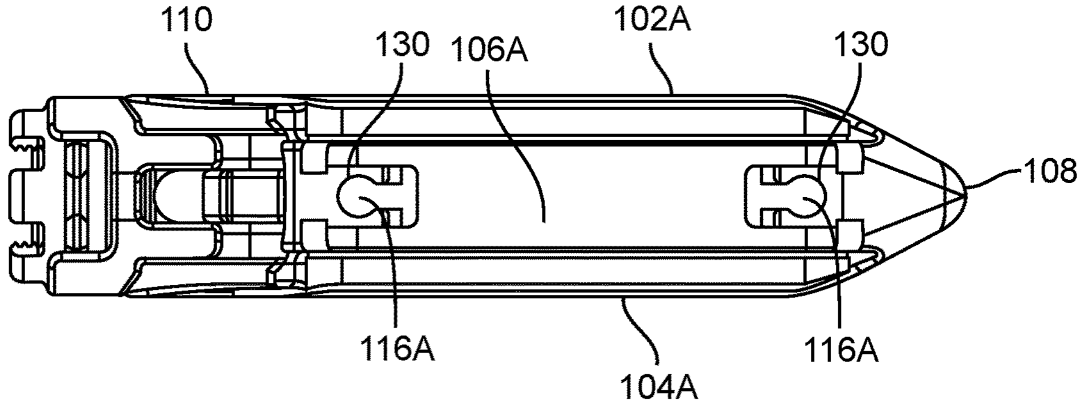

FIG. 6B is a side view of the expandable interbody spacer 100 in the collapsed state showing the upper and lower endplates 102A, 104A, lateral expansion wedge 106A, the frame 108 and the housing 110. Also shown are the vertical expansion shuttles 116A, 116B engaged with the lateral slots 130 of the frame 108 and the housing 110.

Figure 6C:
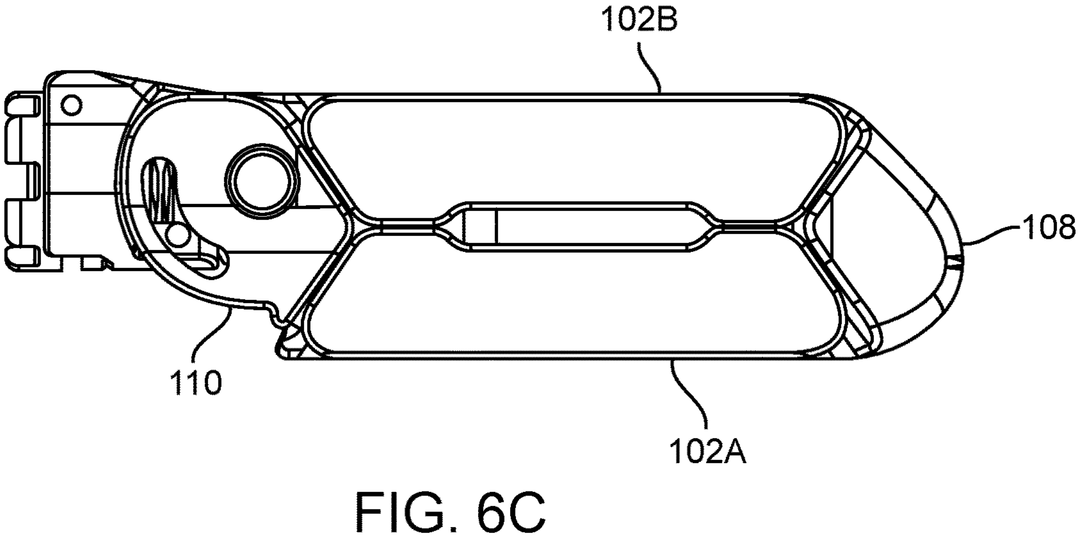

FIG. 6C is a top view of the expandable interbody spacer 100 in the collapsed state showing the upper endplates 102A, 102B, the frame 108 and the housing 110.

Figure 7A:
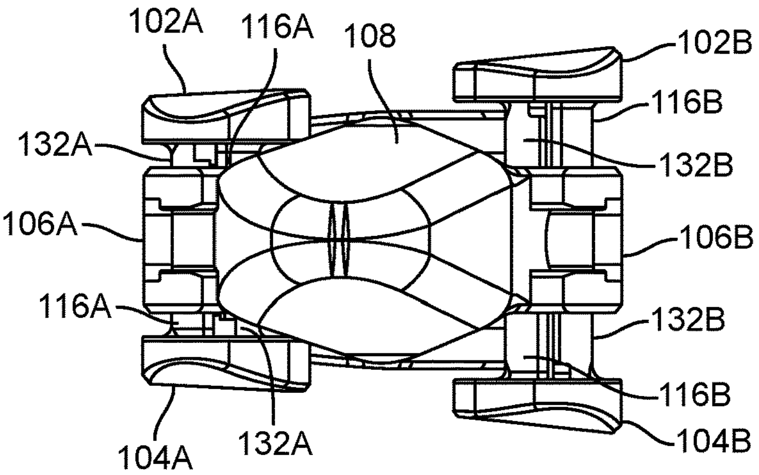
FIGS. 7A-7C show a front view, a side view and a top view of the expandable interbody spacer of FIG. 1 in the expanded state.

FIG. 7A is a front view of the expandable interbody spacer 100 in the expanded state showing the upper endplates 102A, 102B and lower endplates 104A, 104B moved both vertically V and laterally L away from each other, and the upper and lower endplates 102A, 104A and lateral expansion wedge 106A on one side and the upper and lower endplates 102B, 104B and lateral expansion wedge 106B on the other side moved in the lateral L direction away from each other.

Figure 7B:
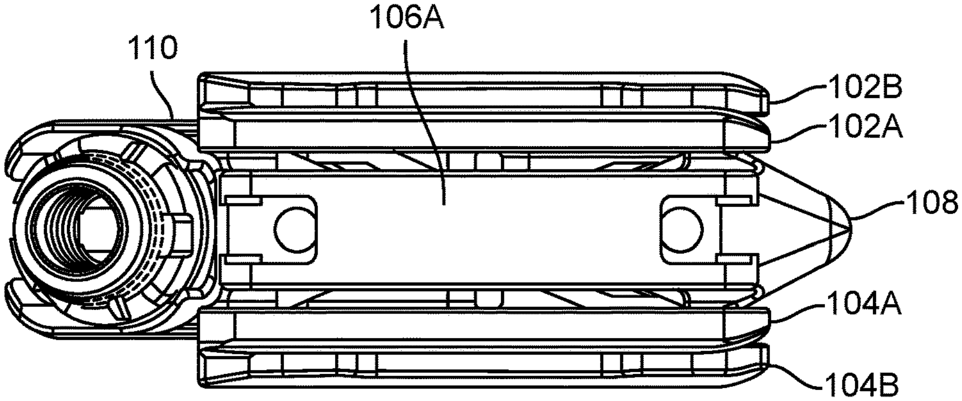

FIG. 7B is a side view of the expandable interbody spacer 100 in the expanded state showing the upper and lower endplates 102A, 102B, the frame 108 and housing 110.

Figure 7C:
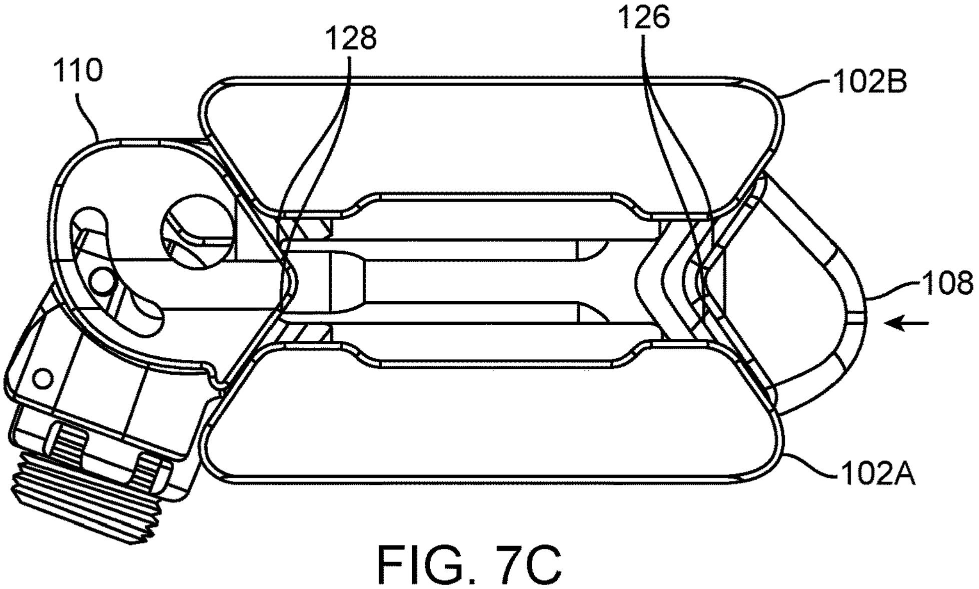

FIG. 7C is a top view of the expandable interbody spacer 100 in the expanded state showing the upper endplates 102A, 102B away from each other, the thread portion of the drive screw 112 engaged with threaded portion of the frame 108. Also shown are the angle ramps 126 on the frame 108 engaging the front ramped ends 127 of the lateral expansion wedges 106A, 106B and the angled ramps 128A, 128B on the housing 110 engaging the rear ramped ends 129 of the lateral expansion wedges 106A, 106B.

While a drive screw is shown, the drive mechanism can be any mechanism capable of moving the frame and housing toward or away from each other or to expand or collapse the expandable interbody spacer. Other types of drive mechanisms may include: a belt drive, rack and pinion drive, linear motor drive, ball screw drive, lead screw drive, or any other suitable drive.

While two upper endplates, two lower endplates and two lateral expansion wedges are in the embodiments shown, other embodiments may include two or more upper endplates, two or more lower endplates or lateral expansion wedges. For example, there may be three upper and lower endplates and lateral expansion wedges, four upper and lower endplates and lateral expansion wedges, etc.

Figure 8A:
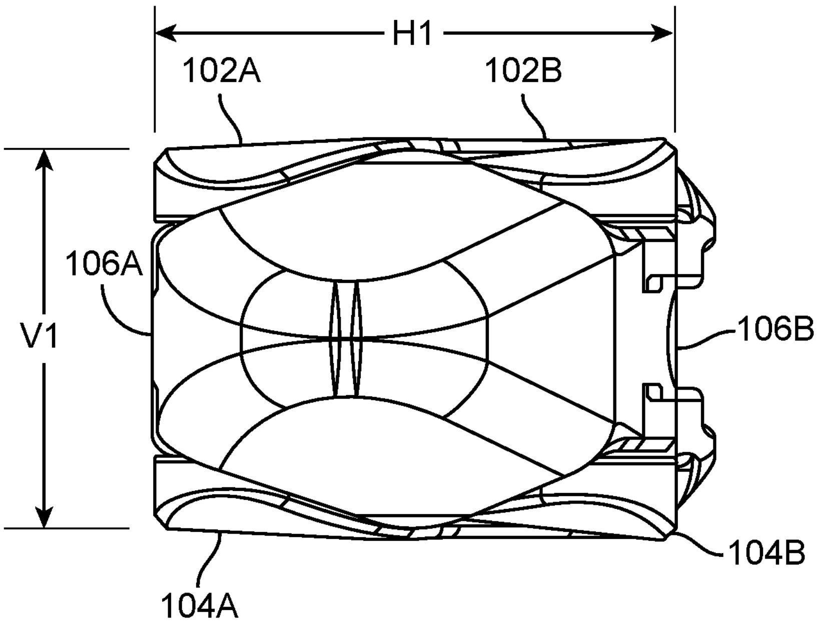
FIGS. 8A and 8B are front views of the expandable interbody spacer in a collapsed state and an expanded state.
Figure 8B:
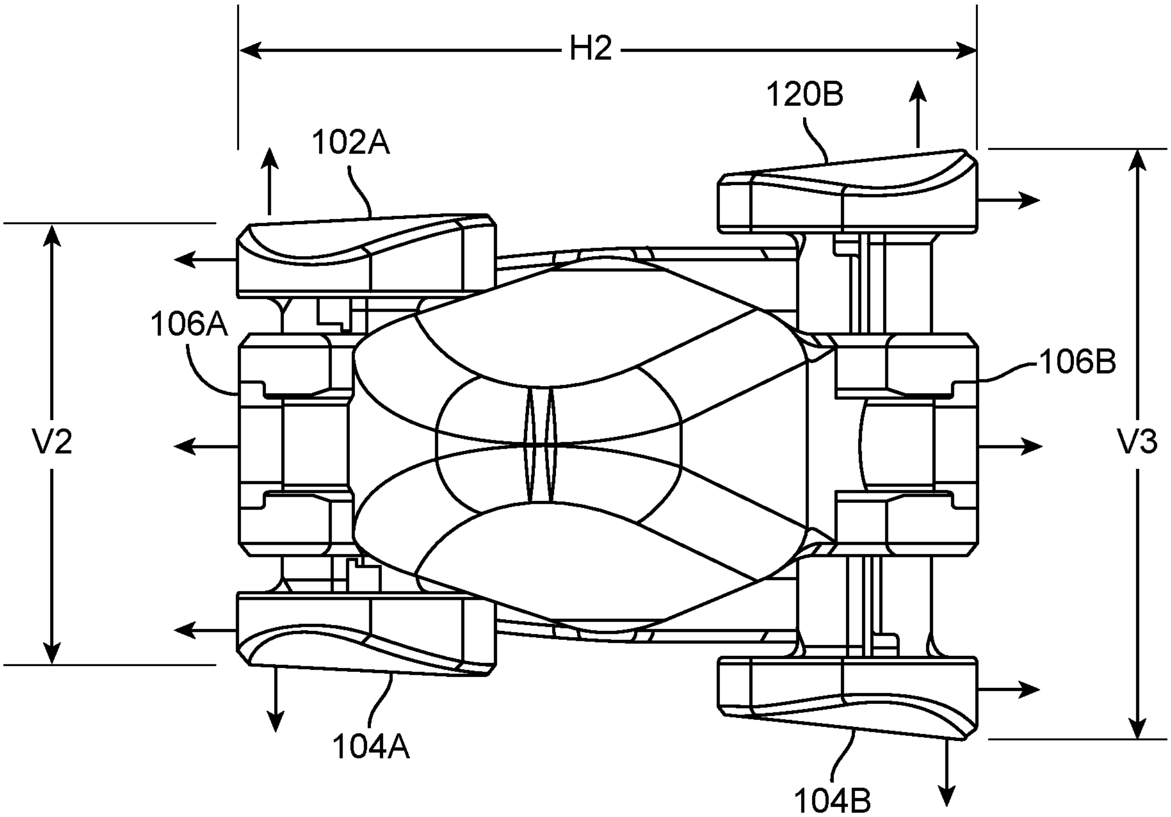

FIGS. 8A and 8B are front views of the expandable interbody spacer 100 in collapsed and expanded states. When the drive screw 112 is turned or rotated in the first direction, the frame 108 and housing 110 move toward each other and closer together, which moves the upper and lower endplates 102A, 102B, 104A, 104B away from each other both vertically and laterally, and the lateral expansion wedges 106A, 106B move away from each other laterally, to expand the expandable interbody spacer 100.

During movement frame 108 and housing 110 toward each other, the single-angle ramps 126 on the frame 108 engage front angled ramp ends 127, and the single-angle ramps 128 on the housing 110 engage the rear angled ramp ends 129, and laterally move the lateral expansion wedges 106A, 106B, the upper and lower endplates 102A, 102B, 104A, 104B and vertical expansion shuttles 116A, 116B.

The design of the ramps between the components allows the upper endplates 102A, 102B and lower endplates 104A, 104B to vertically move away from each other while at the same time the posterior upper and lower endplates 102A, 104A and anterior upper and lower endplates 102B, 104B move laterally away from each other, thereby expanding the expandable interbody spacer 100 both vertically and laterally from the collapsed state (FIG. 8A) to the expanded state (FIG. 8B).

In the collapsed state the expandable interbody spacer 100 has a first vertical height V1 and first lateral width L1. When the drive screw 112 is rotated in a first direction, the frame 108 and housing 110 start moving toward each other and the upper and lower endplates expand to a second vertical and second lateral width. The expandable interbody spacer 100 does not have to be completely extended to the maximum vertical height and can be stopped anywhere between, depending on the expansion needed between the adjacent vertebrae.

In the expanded state the expandable interbody spacer 100 includes a central opening that may be filled with materials, such as bone graft, allograft, Demineralized Bone Matrix ("DBM") or other suitable materials.

The upper and lower endplates 102A, 102B, 104A, 104B may include surface features or treatment configured to promote bone growth that engage the bone. For example, the surface may be a textured surface or roughened surface to promote bone integration or the surface may use a coating or be chemically etched to form a porous or roughened surface. In some embodiments the surface may include teeth. Each of the upper and lower endplates 102A, 102B, 104A, 104B may use the same surface feature or different surface feature.

The expandable interbody spacer 100 components may be fabricated from any biocompatible material suitable for implantation in the human spine, such as metal including, but not limited to, titanium and its alloys, stainless steel, surgical grade plastics, plastic composites, ceramics, bone, or other suitable materials. In some embodiments, surfaces on the components may be formed of a porous material that participates in the growth of bone with the adjacent vertebral bodies. In some embodiments, the components may include a roughened surface that is coated with a porous material, such as a titanium coating, or the material is chemically etched to form pores that participate in the growth of bone with the adjacent vertebra. In some embodiments, only portions of the components be formed of a porous material, coated with a porous material, or chemically etched to form a porous surface, such as the upper and lower surfaces that contact the adjacent vertebra are roughened or porous.

The expandable interbody spacer 100 may also be used with various tools, such as inserter tools, deployment tools and/or removal tools. The tools may include various attachment features to enable percutaneous insertion of the expandable interbody spacer 100 into the patient. For example, the tools may include arms or clamps to attach to the cutouts or other openings, slots or trenches of the drive mechanism. The tools may also include an actuation device to couple with the rear section of the screw 112. Once the expandable interbody spacer 100 has been inserted and positioned within the intervertebral space between two vertebrae with the insertion tool, the deployment tool may actuate to deploy and expand the expandable interbody spacer 100 by applying a rotational force to screw 112.

In operation, the expandable interbody spacer 100 may be inserted into the intervertebral disc space between two vertebrae using an insertion tool. In some cases, the disc space may include a degenerated disc or other disorder that may require a partial or complete discectomy prior to insertion of the expandable interbody spacer 100. The deployment tool may engage with the rear end of the expandable interbody spacer 100. As the deployment tool applies the rotational force, the expandable interbody spacer 100 gradually expands as described above. The insertion tool is then removed or uncoupled from the expandable interbody spacer 100.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. An expandable interbody spacer for placement between adjacent vertebrae comprising:

a housing having lateral housing ramps, lateral housing slots and radial slots;

an articulation component rotatably coupled with the radial slots, a frame having lateral frame ramps, lateral frame slots, and a central strut with an angled slot having an angled face;

an articulating drive screw coupled with the angled slot via pivot pins, the articulating drive screw being captured within the articulation component; and a drive nut coupled to the articulating drive screw, wherein advancing the drive nut on the drive screw causes the drive screw to translate rearward relative to the housing and induce axial compression on the frame relative to the housing when the articulation component is in an axial state, and the pivot pins are configured to contact the frame slot at such an angle as to produce direct axial translation;

wherein the direct axial translation by the articulating drive screw will axially translate the frame and housing toward each other inducing lateral expansion of left and right lateral expansion wedges to move away from each other, which also moves left and right proximal vertical expansion shuttles away from each other, while simultaneously, axially translating the proximal vertical expansion shuttles toward distal vertical expansion shuttles, inducing both lateral expansion and vertical expansion of upper and lower endplates from a collapsed state to an expanded state.

2. An expandable interbody spacer for placement between adjacent vertebrae comprising:

a housing having lateral housing ramps, lateral housing slots and radial slots;

an articulation component rotatably coupled with the radial slots, a frame having lateral frame ramps, lateral frame slots, and a central strut with an angled slot having an angled face;

an articulating drive screw coupled with the angled slot via pivot pins, the articulating drive screw being captured within the articulation component; and a drive nut coupled to the articulating drive screw, wherein advancing the drive nut on the drive screw causes the drive screw to translate rearward relative to the housing and induce axial compression on the frame relative to the housing when the articulation component is in an articulated state, and the pivot pins are configured to contact the angled face of the frame, translation of the pins along the angled face will induce axial compression of the frame relative to the housing;

wherein the axial compression by the articulating drive screw will axially translate the frame and housing toward each other inducing lateral expansion of left and right lateral expansion wedges to move away from each other, which also moves left and right proximal vertical expansion shuttles away from each other, while simultaneously, axially translating the proximal vertical expansion shuttles toward distal vertical expansion shuttles, inducing both lateral expansion and vertical expansion of upper and lower endplates from a collapsed state to an expanded state.

3. An expandable interbody spacer for placement between adjacent vertebrae comprising:

a housing having lateral housing ramps, lateral housing slots and radial slots;

an articulation component rotatably coupled with the radial slots, a frame having lateral frame ramps, lateral frame slots, and a central strut with an angled slot having an angled face;

an articulating drive screw coupled with the angled slot via pivot pins, the articulating drive screw being captured within the articulation component;

a drive nut coupled to the articulating drive screw, wherein advancing the drive nut on the drive screw causes the drive screw to translate rearward relative to the housing and induce axial compression on the frame relative to the housing via two different methods:

in a first method, when the articulation component is in an axial state, and the pivot pins are configured to contact the frame slot at such an angle as to produce direct axial translation; or in a second method, when the articulation component is in an articulated state, and the pivot pins are configured to instead contact the angled face of the frame, translation of the pins along the angled face will induce axial compression of the frame relative to the housing;

left and right lateral expansion wedges having lateral wedge ramps slidingly engaged with the lateral frame ramp and the lateral housing ramp;

left and right proximal expansion shuttles having lateral protrusions slidingly coupled to the lateral housing slots and proximal vertical shuttle ramps coupled to left and right lateral expansion wedges;

left and right distal expansion shuttles having lateral protrusions slidingly coupled to the lateral frame slots and distal vertical shuttle ramps are coupled to left and right lateral expansion wedges;

left and right upper endplates having proximal and distal vertical endplate ramped features, the proximal vertical endplate ramped features are slidingly engaged with the proximal vertical shuttle ramps and the distal vertical endplate ramped features are slidingly engaged with the distal vertical shuttle ramps;

left and right lower endplates having proximal and distal vertical endplate ramped features, the proximal vertical endplate ramped features are slidingly engaged with the proximal vertical shuttle ramps and the distal vertical endplate ramped features are slidingly engaged with the distal vertical shuttle ramps;

wherein the direct axial translation or the angled axial compression by the articulating drive screw will axially translate the frame and housing toward each other inducing lateral expansion of left and right lateral expansion wedges to move away from each other, which also moves left and right proximal vertical expansion shuttles away from each other, while simultaneously, axially translating the proximal vertical shuttle ramps toward distal vertical shuttle ramps, inducing both lateral expansion and vertical expansion of upper and lower endplates from a collapsed state to an expanded state.

* * * * *